United States Patent [19]

Straith

[11] Patent Number: 4,553,540

[45] Date of Patent: Nov. 19, 1985

[54] AIRWAY

[76] Inventor: Richard E. Straith, 17100 W. 12 Mile Rd., Southfield, Mich. 48076

[21] Appl. No.: 523,707

[22] Filed: Aug. 16, 1983

[51] Int. Cl.⁴ .................... A61M 29/00; A61M 16/00
[52] U.S. Cl. ............................. 128/200.26; 128/207.14
[58] Field of Search ...................... 128/207.14, 207.15, 128/200.26, 17, 20

[56] References Cited

U.S. PATENT DOCUMENTS

| | | | |
|---|---|---|---|
| 2,127,215 | 8/1938 | Gwathmey | 128/207.14 |
| 2,599,521 | 6/1952 | Berman | 128/207.14 |
| 2,756,742 | 7/1956 | Barton | 128/207.14 |
| 3,306,298 | 2/1967 | Raimo | 128/207.14 |
| 3,398,797 | 8/1968 | Raimo | 128/207.14 |
| 3,756,244 | 9/1973 | Kinnear et al. | 128/207.14 |
| 3,774,616 | 11/1973 | White et al. | 128/200.26 |
| 3,908,665 | 9/1975 | Moses | 128/207.14 |
| 3,926,196 | 12/1975 | Bornhorst et al. | 128/207.14 |
| 3,930,507 | 1/1976 | Berman | 128/207.14 |
| 4,054,135 | 10/1977 | Berman | 128/200.26 |
| 4,112,936 | 9/1978 | Blachly | 128/207.14 |
| 4,198,967 | 4/1980 | Dror | 128/207.14 |
| 4,356,821 | 11/1982 | Rind | 128/207.14 |
| 4,363,320 | 12/1982 | Kossoue | 128/200.26 |
| 4,365,625 | 12/1982 | Rind | 128/207.14 |

Primary Examiner—Henry J. Recla
Assistant Examiner—Karin M. Reichle
Attorney, Agent, or Firm—Harness, Dickey & Pierce

[57] ABSTRACT

An airway having a pair of elongate generally parallel body members guided and restrained for limited longitudinal sliding motion of one member relative to the other, hingedly interconnected at the inner ends thereof to a tongue clamping member, and provided at the outer ends thereof with manual actuators at least one of which has a lateral extension that abuts against the face of a patient when the airway is inserted into the mouth, the body members being curved to conform at least generally to the tongue of the patient and the clamping member being adapted to extend into the throat of the patient when the airway is fully inserted, whereby manipulation of the body members in one direction acts through the hinges to rock the clamping member toward the front of the throat and into pressed engagement with the tongue to compress the same forwardly and whereby manipulation of the body members in the opposite direction rocks the clamping member toward the back of the throat to release the tongue and permit removal of the airway from the mouth.

10 Claims, 7 Drawing Figures

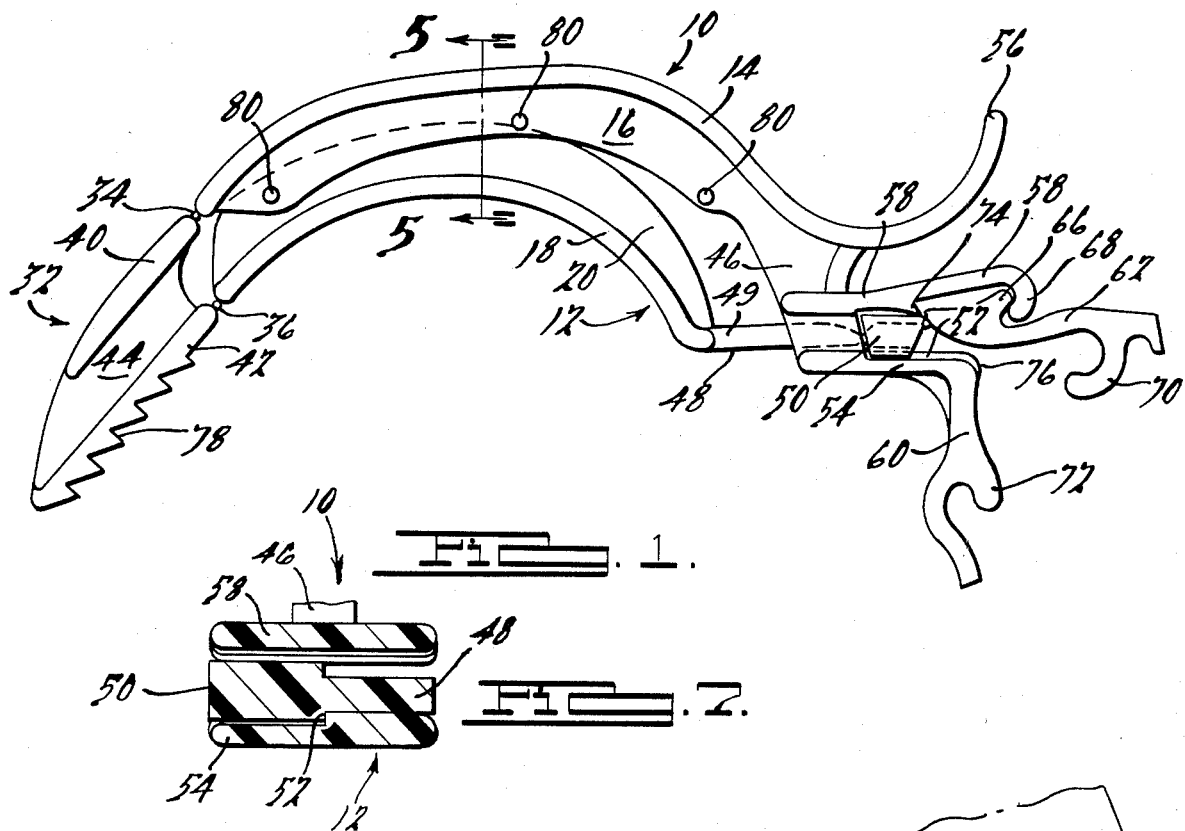
FIG. 1.
FIG. 2.
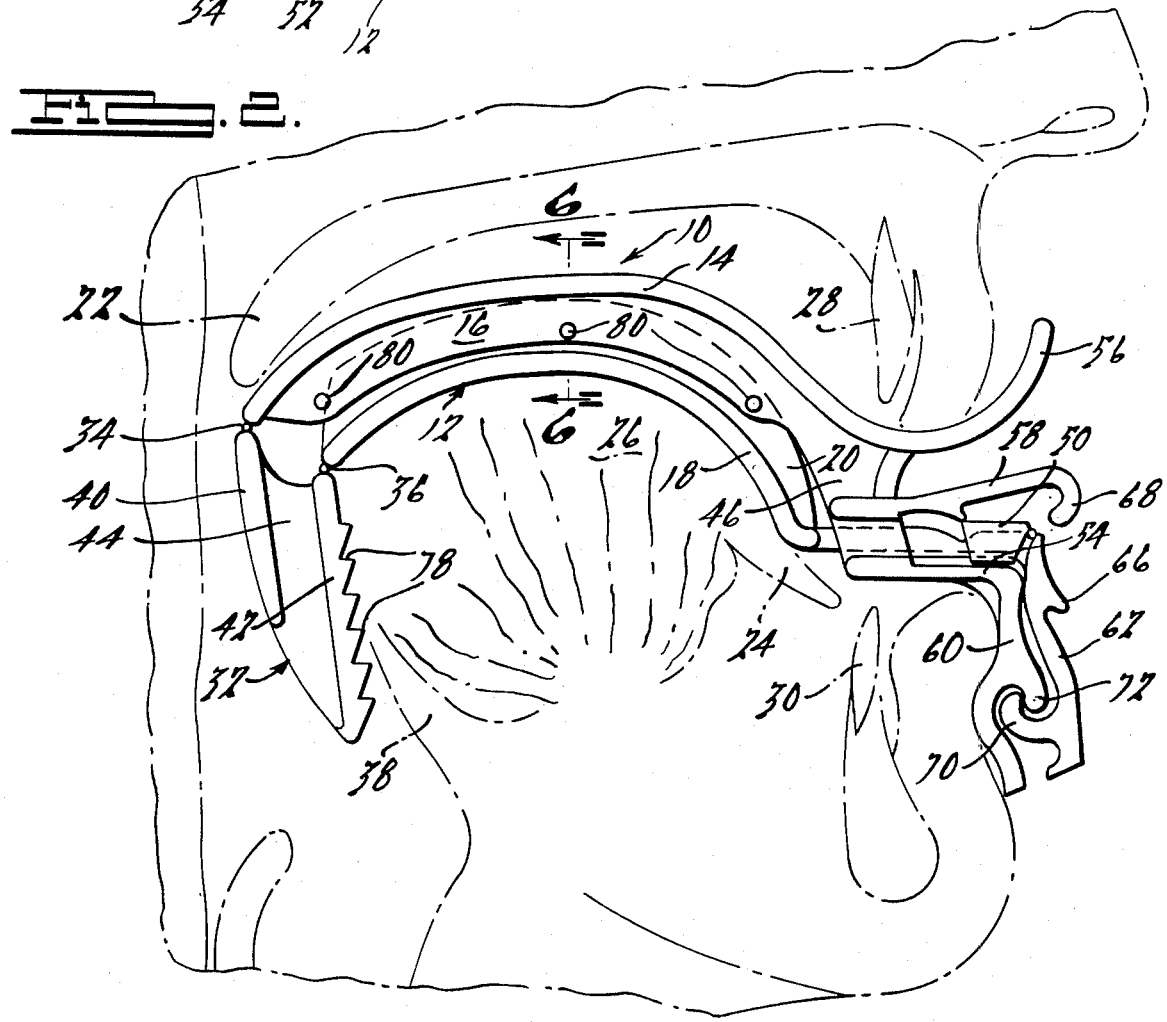
FIG. 3.

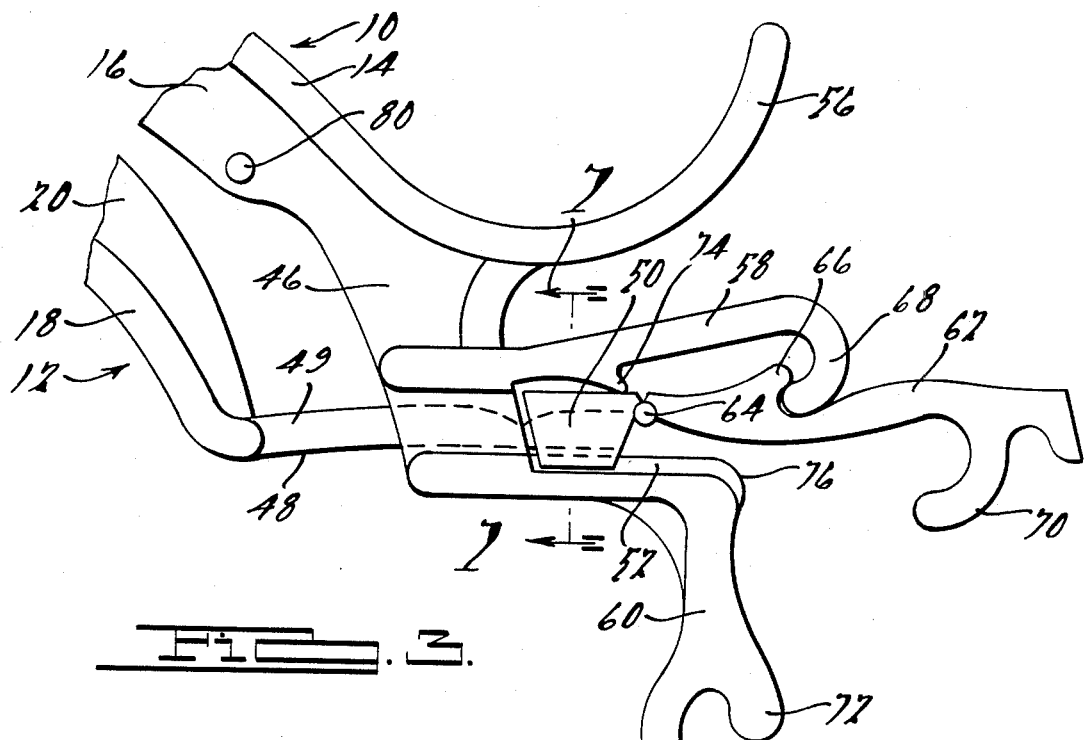
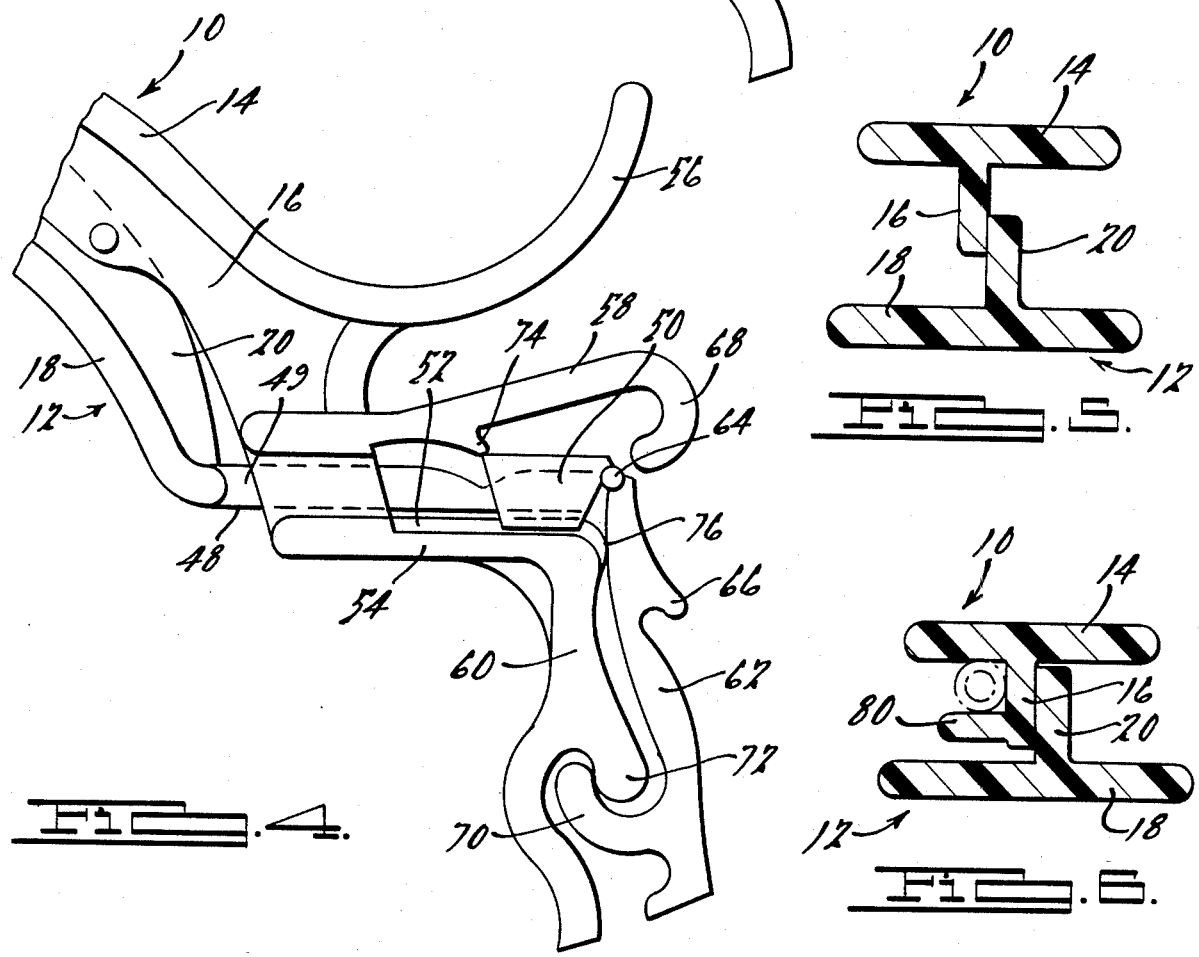

AIRWAY

BACKGROUND OF THE INVENTION

The present invention relates to oral airways of the type adapted for use wherever and whenever it is necessary to prevent a patient's tongue from falling back into the throat and obstructing the flow of air to the lungs as, for example, when anesthetic is being or has been administered to the patient. Also, airways of this type are sometimes formed to provide a passage through which an aspirator or oxygen tube can be passed into the esophagus or trachea of the patient as required by the circumstances attending the use of the airway.

Typical examples of prior art airways are disclosed by the patents listed below:

| Patent No. | Inventor | Issued |
|---|---|---|
| 2,127,215 | Gwathmey | 8/16/38 |
| 2,599,521 | Berman | 6/3/52 |
| 3,306,298 | Raimo | 2/28/67 |
| 3,398,747 | Raimo | 8/27/68 |
| 3,756,244 | Kinnear et al | 9/4/73 |
| 3,908,665 | Moses | 9/30/75 |
| 3,926,196 | Bornhorst et al | 12/16/75 |
| 3,930,507 | Berman | 1/6/76 |
| 4,054,135 | Berman | 10/18/77 |
| 4,112,936 | Blachly | 9/12/78 |
| 4,196,724 | Wirt et al | 4/8/80 |
| 4,198,967 | Dror | 4/22/80 |

All of the airways known to applicant, including those disclosed by the patents listed above, are adapted to be used by introducing the airway manually into the mouth of the patient and then holding it in some way so that it does not interfere with surgical operations or other treatment being performed on the patient. However, these airways have in common the disadvantage that they can be displaced by the tongue which results in the airway being obstructed by the tongue in certain situations.

SUMMARY OF THE INVENTION

The present invention provides an airway of the above mentioned character having an abutment portion at the forward end thereof that seats rearwardly against the patient's face adjacent to the mouth to limit inward movement of the airway during insertion thereof and provided also with a pivoted clamping member at the inner end thereof that can be manipulated manually from the forward or outer end of the airway and exteriorly of the patient's mouth and swung or rocked selectively forwardly toward the front of the patient's throat or rearwardly toward the back of the throat. When the airway is fully inserted, the clamping member projects into the throat angularly toward the back thereof at the base of the tongue. When the clamping member is swung forwardly in the manner described above, it presses against and clampingly engages the base of the tongue urging the latter forwardly and exerting a rearward force on the airway that pulls the abutment portion thereof firmly against the face. As a result, the patient's tongue is confined between the clamping member and the front portion of the curved section of the lower body member 12 to hold the tongue forwardly in the patient's mouth and to retain the airway in the clamped position in a manner that eliminates inadvertent displacement by the tongue and the necessity of holding the airway manually in place. If necessary or desirable, the clamping member may be provided with serrations or other means for preventing the clamping member from inadvertently sliding on and releasing the tongue while in the clamped position. Conversely, the clamping member can be swung toward the rear of the throat from the forward or outer end of the airway; and, as the clamping member swings away from the tongue it releases the latter sufficiently to permit ready removal of the airway from the patient's mouth.

DESCRIPTION OF THE DRAWINGS

FIG. 1 is a side elevational view of an airway embodying the present invention and showing the clamping member in the rearward or tongue-releasing position;

FIG. 2 is a view similar to FIG. 1 but showing the airway fully inserted into the mouth of a patient and the clamping member in the forward or clamping position;

FIG. 3 is an enlarged, fragmentary, side elevational view showing the forward portion of the airway with the parts thereof positioned as illustrated in FIG. 1;

FIG. 4 is a view similar to FIG. 3 but showing parts of the airway positioned as illustrated in FIG. 2;

FIG. 5 is an enlarged, transverse sectional view taken on the line 5—5 of FIG. 1;

FIG. 6 is an enlarged, transverse sectional view taken on the line 6—6 of FIG. 2; and FIG. 7 is an enlarged, transverse sectional view taken on the line 7—7 of FIG. 3.

DESCRIPTION OF THE PREFERRED EMBODIMENT

As a special feature of this invention, the instant airway is uniquely formed so that it can be injection molded inexpensively in one piece of a suitable plastic resin material. Also, the airway is uniquely constructed so that, when it is fully inserted into the mouth of the patient, the clamping member at the inner end thereof can be manipulated manually entirely from the forward end of the airway and outside the patient's mouth to clamp and hold the tongue and the clamping member locked securely in the clamped position so that the airway alone will continue to hold the tongue until the clamping member is released. In this connection, the means for manipulating the clamping member also can be released manually entirely from the outer end of the airway and from a position outside the patient's mouth to swing the clamping member toward the rear of the throat and away from the patient's tongue and then locked in the released position so as not to interfere with removal of the airway. All of these operations can be performed easily and quickly from the forward end of the airway and without necessity of the person performing the operations having to put his hands or any portions thereof in the patient's mouth either to insert or to remove the airway or to hold the same in place during the time the airway remains in the mouth.

More particularly, the airway of this invention comprises upper and lower body members 10 and 12 arranged in generally parallel relation, as perhaps best shown in FIGS. 1 and 2. In the particular form of the invention here shown by way of illustration, the body members 10 and 12 are generally T-shaped in transverse section, the upper body member 10 having a horizontal flange 14 provided at substantially the middle thereof with a depending web 16 and the lower body member 12 having a horizontal flange 18 provided with a medianly disposed upstanding web 20 that normally overlaps the web 16 along a substantial portion of its length. In the preferred form of the invention, the two webs 16 and 20 are offset in opposite directions from the center lines of their respective flanges 14 and 18, as shown in FIG. 5, so that the body members 10 and 12 are centered with respect to each other. Although the upper body member 10 is capable of being moved angularly with respect to the lower body member 12, as shown in FIG. 1, in the normal use and operation of the airway, the two body members normally are disposed in generally parallel relation each with respect to the other as is literally true, for example, when the clamping member previously referred to is disposed and locked in the clamped position, as shown in FIG. 2. Both of the body members 10 and 12 are of elongate configuration, and they are longitudinally curved so that, in the fully inserted position of the airway, they conform at least generally to the top surface of the patient's tongue. Since the upper body member 10 is superimposed on the lower body member 12, it does not physically contact the tongue; but, in use, the lower body member 12 overlays the tongue with the flange 18 thereof in direct contact with the top of the tongue. Also, as clearly shown in the drawing, the body members 10 and 12 are sufficiently long so that, when the airway is fully inserted, the inner ends of the body members are disposed at or slightly beyond the soft pallet 22 and the forward or outer ends thereof are disposed substantially at the tip 24 of the tongue 26 adjacent to the teeth 28 and 30.

The clamping member 32 at the inner ends of the two body members 10 and 12 is hingedly connected to the latter by a pair of integral hinges 34 and 36, respectively. As clearly shown in the drawing, the clamping member 32 is of elongate configuration and extends from the body members 10 and 12 essentially as a continuation thereof so as to project into the throat and, in at least one position thereof, as hereinafter explained, to overlay the base of the tongue 26 and perhaps also at least partially to overlap at least the tip of the epiglottis 38, as shown in FIG. 2. The particular clamping member 32 here shown is formed with upper and lower longitudinal flanges 40 and 42 joined by a medianly disposed web 44; and it is longitudinally tapered toward the free end thereof so as to slip readily into the throat when the airway is inserted into the mouth of the patient. The adjacent ends of the two flanges 14 and 40 are tapered slightly and integrally joined by a flexible web of the plastic material from which the airway is made to form the hinge 34. Similarly, the adjacent ends of the flanges 18 and 42 are tapered and joined by a thin flexible web of plastic material to form the hinge 36. Thus, the two hinges 34 and 36 are spaced transversely of the airway so that when the lower body member 12 is moved inwardly longitudinally with respect to the upper body member 10, the lower hinge 36 is advanced to pivot or rock the clamping member 32 about the hinge 34, with the result that the clamping member is moved from the position shown in FIG. 2 to the position shown in FIG. 1. Conversely, if the lower body member 12 is moved outwardly longitudinally with respect to the upper body member 10, the lower hinge 36 is retracted to pivot the clamping member 32 counterclockwise about the hinge 34 from the position shown in FIG. 1 to the position shown in FIG. 2.

At the forward outer ends of the body members 10 and 12, the web 16 of the upper body member 10 extends angularly forwardly and downwardly, as at 46, and across a forward extension 48 of the flange 18. The two extensions 46 and 48 cross almost at right angles with respect to each other, as shown in FIGS. 3 and 4; and the near portion of the flange 18, as viewed in FIGS. 3 and 4, is cut away as at 49 to accommodate the web extension 46. The extension 48 also is formed at the forward end of the cutout 49 with a guide block 50 that projects below the extension 48 and overlaps an elongate longitudinal shoulder 52 provided on a forwardly extending portion 54 of the web extension 46 at the lower end of the latter.

In view of the foregoing, it will be readily apparent that the flange extension 48 passes behind the web extension 46 as viewed in FIG. 3 to limit movement of the flange extension 48 to the left, as viewed in FIG. 7; and the guide block 50 seats against the shoulder 52 to limit movement of the flange extension 48 to the right, as viewed in FIG. 7, so that the web extension 46 and the shoulder 52 mutually cooperate to prevent lateral separation of the body members at the forward ends thereof while at the same time permitting the forward ends of the body members, and consequently the body member 12, to move longitudinally with respect to the other body member 10. It is contemplated that the side of the web extension 46 engaged by the flange extension 48 and the shoulder 52 be spaced laterally sufficiently to permit free longitudinal movement of the flange extension 48 and consequently of the lower body member 12.

At its outer end, the flange 14 is formed with a forwardly and upwardly curved extension 56 that provides a convenient hand-hold or handle by means of which the airway can be grasped and held manually when the airway is inserted into the mouth or removed therefrom and during longitudinal sliding movement of the lower body member 12 with respect to the upper body member 10.

Manifestly, inward sliding movement of the lower body member 12 relative to the upper body member 10; viz., to the left as viewed in the drawings, swings the clamping member 32 clockwise on the hinge 34 and positions the clamping member as shown in FIG. 1 when the lower body member 12 is fully advanced. In this connection, it will be observed that the lower body member 12 can be advanced or moved inwardly relative to the upper body member 10 only until the guide block 50 engages the forward or outer edge of the web extension 46. On the other hand, when the lower body member 12 is moved forwardly or outwardly with respect to the upper body member 10 to pivot the clamping member 32 counterclockwise on the hinge 34, forward movement of the lower body member 12 is limited by engagement of the flange 18 with the web extension 46 at the inner end of the cutout 49. At the outward limit of its travel, the lower body member 12 positions the clamping member 32, as shown in FIG. 2, at the extreme limit of its counterclockwise respective movement about the hinge 34.

In order to hold the lower body member 12 at the inner and outer limits of its horizontal sliding movement relative to the upper body member 10, the extension 46 of the web 16 is formed with a forwardly extending flange member 58 that is disposed substantially parallel to the member 54 and above the forward extension 48 so that the latter slides back and forth between the two members 54 and 58. At the forward end of the forwardly extending portion 54 is a substantially right angularly extending depending tab 60; and at the extreme forward or outer end of the forward extension 48 is a latch member 62 that is joined thereto by an integral hinge 64 which is formed similarly to the hinges 34 and 36 previously referred to.

In the extreme rearward position of the lower body member 12, shown in FIG. 3, the hinge 64 is disposed substantially behind or rearwardly of the forward or outer end of the extension 54 which in turn is disposed substantially behind or rearwardly of the extreme forward end of the flange member 58. In the extreme outer position of the lower body member 12, shown in FIG. 4, the hinge 64 is disposed slightly beyond or forwardly of the outer end of the extension 54 and slightly rearwardly of or behind the forward end of the flange member 58. Also, in the extreme rearward position of the lower body member 12, a transverse rib 66 formed on the outer face of the latch member 62 substantially midway between the inner and outer ends thereof, engages behind a downwardly and rearwardly curved catch 68 formed on the end of the flange member 58; and in the extreme outer or forward position of the lower body member 12, a latching transverse rib 70 formed on the undersurface of the latch member 62 adjacent the outer end thereof engages behind a catch 72 formed on the outer face of the tab 60. In both positions of the lower body member 12, the latching ribs 66 and 70 engage behind respective catches 68 and 72 with a snap action.

In practice, the lower body member 12 is advanced; viz., moved inwardly with respect to the upper body member 10 by pushing on the latch member 62 with the latter disposed substantially horizontally or in-line with the forward extension 48, as shown in FIGS. 1 and 3. As suggested, advancement of the lower body member 12 in this manner swings the clamping member 32 clockwise to the position shown in FIG. 1 which prepares the airway for insertion into the mouth of the patient. During inward movement of the lower body member 12, a transverse rib 74 on the underside of the flange member 58 rides on the top surface of the guide block 50 to hold the latter downwardly against the forwardly extending portion 54 to assure butting engagement between the guide block 50 and the shoulder 52. This butting engagement between the block 50 and the shoulder 52 at one side of the web extension 46 and the overlapping engagement of the web 20 on the other side of the web 16 in combination with the hinges 34 and 36 at the inner end of the airway holds the two body members 10 and 12 in proper sliding association with each other; viz., so that the lower body member 12 is free to slide relative to the upper body member 10.

When the lower body member 12 approaches the normal limit of its inward travel and just before the guide block 50 engages the downward extension 46, the latching rib 66 moves into position with respect to the catch 68 such that the latch can be snapped behind the catch, as shown in FIGS. 1 and 3. If the airway is molded from plastic resin material, the latter is sufficiently flexible and resilient so that the latching rib can be readily snapped into position behind the catch; however, at the same time, the material is sufficiently stiff so that the catch holds the latching rib securely during normal handling and manipulation of the airway.

Contrariwise, when it is desired to retract the lower body member 12 with respect to the upper body member 10; viz., to move it outwardly, the latching member 62 is first pushed downwardly about the hinge 64 to disengage the latching rib 66 from the catch 68 and then swung downwardly to engage the latching member with the outer end surface 76 of the forward extension 54. Thereafter, the surface 76 serves as a fulcrum about which the latch member 62 turns; and, as the downward swinging action of the latch member 62 progresses, it acts against the fulcrum 76 to retract the lower body member 12. As suggested, retractive or outward movement of the lower body member 12 swings the clamping member 32 counterclockwise on the two hinges 34 and 36 to the clamped position shown in FIG. 2.

In the unclamped or extended position shown in FIG. 1, the clamping member 32 is disposed properly to enter the throat as the airway is inserted fully to a position where the tab 60 engages and lays against the lower lip of the patient; and, as the clamping member swings counterclockwise in the manner previously described, it moves toward the front of the throat and eventually assumes a downwardly and slightly forwardly inclined position, as shown in FIG. 2. In the latter position of the clamping member 32, it presses the tab 60 firmly against the patient's lip and securely holds the patient's tongue forward in the mouth. If necessary or desirable, the forward face of the clamping member 32 may be formed with transverse ribs or teeth 78 that embed in the base of the tongue and perhaps also in the tip portion of the epiglottis to prevent the clamping member 32 from slipping upwardly and inadvertently releasing the tongue. In any event, as the clamping member 32 approaches the limit of its counterclockwise travel, the latching rib 70 contacts the catch 72 just behind the lip of the latter and is readily snapped into position behind the catch by continued downward and inward pressure against the latch member 62. Thereafter, the airway will remain securely in the fully inserted position, as shown in the drawing, to hold the patient's tongue and to prevent it from falling back into the patient's throat until the latch member 62 is pulled outwardly to release the latching rib 70 from the catch 72. Continued upward pivotal movement of the released latch member 62 returns it to a straight or horizontal position in which the lower body member 12 can be pushed inwardly to return the clamping member 32 to the FIG. 1 position in the manner hereinabove described preparatory to removal of the airway from the patient's mouth.

During the movements described above, the handle 56 and the flange members 54 and 58, including the tab 60 and the latch member 62, are accessible for manual manipulation of the airway as required to perform the insertion and removal of the airway and the clamping and unclamping motions of the member 32.

Formed on and extending laterally from the web 16 of the upper body member 10 adjacent to the free edge of the web are a plurality of longitudinally spaced pins 80 that, in combination with the overhanging portion of the flange 14, define a way through which a tube can be inserted into the throat of the patient after the airway has been inserted and clamped in position. The tube, of course, is inserted from the outer end of the airway; and, after it passes over the top of the foremost pin 80, the overhanging portion of the flange 14 serves as a guide to direct the tube over the other two pins 80 and into the aligned channel defined by the flanges 40 and 42 of the clamping member 32. When the clamping member 32 is in the unclamped position shown in FIG. 1, the clamping member is positioned to direct the tube into the esophagus if that is required. Alternatively, the tube can be stopped at the entrance to the trachea if that is necessary, as in the case where the tube is used to supply oxygen to the lungs or to administer an anesthetic.

I claim:

1. A tongue retracting airway comprising elongate upper and lower body members disposed in generally parallel relation closely adjacent to each other and having substantially coterminous inner and outer end portions, said body members being adapted to be manually inserted in superimposed orientation into the mouth of an individual and similarly removed therefrom, and adapted further to overlay the tongue of such individual in the inserted position and being longitudinally curved to conform at least generally to the top surface of the tongue;

extensions on the outer end portions of said body members of sufficient length to project from the mouth when said body members are fully inserted, at least one of said extensions having a laterally extending portion disposed to bear on the face of said individual in said fully inserted position to limit further insertion thereof;

an elongate clamping member disposed longitudinally beyond the inner end portions of said body members;

a pair of spaced hinge means spaced transversely with respect to the length of said airway, both of said hinge means being connected to said clamping member and each being connected to a respective one of said body members at the inner end of the latter whereby said clamping member extends into the throat of said individual in the fully inserted position of said airway;

means holding and guiding said body members for limited longitudinal sliding movement of one body member relative to the other of said body members; and manually operable actuator means cooperable with said body members in the fully inserted position of said airway for sliding said one body member longitudinally back-and-forth relative to the other of said body members, said clamping member being connected to said body members by said hinge means such that sliding movement of said one body member in one direction with respect to the other acts through said hinge means to swing said clamping member to a nonaligned position with respect to said body members and toward the front of the throat and into pressed engagement with the latter at the base of the tongue to compress the latter forwardly, and sliding movement of said one body member in the opposite direction with respect to the other acts through said hinge means to swing said clamping member to an aligned position with respect to said body members and toward the back of the throat to release said tongue and to permit ready removal of said airway.

2. An airway according to claim 1 wherein said manually operable actuator means includes latch means for detachably fastening and holding said one body member at at least one limit of its longitudinal movement with respect to the other of said body members in at least one direction.

3. An airway according to claim 1 wherein said manually operable actuator means includes latch means for detachably fastening and holding said one body member at the limits of its travel in both directions with respect to the other body member.

4. An airway according to claim 3 wherein said latch means further comprises a pivoted latch member on the outer end portion of and movable with said one body member, and catch members spaced along the length of the other of said body members separately and detachably engageable with said latch member at the opposite limits of travel of said one body member.

5. An airway according to claim 4 further including fulcrum means on said other body member engageable by said latch member and operable by such engagement and by pivotal movement of said latch member thereon to move said one body member in at least one direction of its longitudinal travel.

6. An airway according to claim 4 wherein said manual operable actuator means further comprises single grip means on said other body member for use in manual actuation of said latch member into and out of engagement with said catch members.

7. An airway according to claim 1 including means on said clamping member adapted to embed itself at least partially in the throat as a result of pressure exerted thereagainst by said clamping member and operative as a result of such embedding engagement to resist withdrawal of said airway.

8. An airway according to claim 1 wherein said guide means includes longitudinally spaced shoulders on each of said body members, the shoulders on one body member facing in an opposite direction to the shoulders on the other body member and in opposed confronting relation with respect to each other and mutually cooperating with each other to restrain longitudinal movement between said body members to an essentially straight line motion.

9. An airway according to claim 8
wherein said airway includes means for inhibiting movement of said body members laterally away from each other.

10. An airway according to claims 1 or 8 wherein said airway is formed in one piece of plastic resin material.

* * * * *